US012502341B2

(12) United States Patent
Jeanne-Rose et al.

(10) Patent No.: US 12,502,341 B2
(45) **Date of Patent: *Dec. 23, 2025**

(54) METHOD FOR THE COSMETIC TREATMENT OF KERATIN MATERIALS EMPLOYING A RARE EARTH METAL COMPOSITION AND AN ALKALINE COMPOSITION

(71) Applicant: L'OREAL, Paris (FR)

(72) Inventors: Valérie Jeanne-Rose, Aulnay-sous-Bois (FR); Henri Samain, Chevilly-Larue (FR)

(73) Assignee: L'Oreal, Paris (FR)

( * ) Notice: Subject to any disclaimer, the term of this patent is extended or adjusted under 35 U.S.C. 154(b) by 750 days.

This patent is subject to a terminal disclaimer.

(21) Appl. No.: 17/786,439

(22) PCT Filed: Dec. 17, 2020

(86) PCT No.: PCT/EP2020/086704
§ 371 (c)(1),
(2) Date: Jun. 16, 2022

(87) PCT Pub. No.: WO2021/122946
PCT Pub. Date: Jun. 24, 2021

(65) Prior Publication Data

US 2023/0032589 A1 Feb. 2, 2023

(30) Foreign Application Priority Data

Dec. 20, 2019 (FR) ...................................... 1915313

(51) Int. Cl.

| | |
|---|---|
| ***A61K 8/365*** | (2006.01) |
| ***A61K 8/20*** | (2006.01) |
| ***A61K 8/41*** | (2006.01) |
| ***A61Q 1/00*** | (2006.01) |
| ***A61Q 5/06*** | (2006.01) |
| ***A61Q 17/04*** | (2006.01) |

(52) U.S. Cl.
CPC ................ *A61K 8/365* (2013.01); *A61K 8/20* (2013.01); *A61K 8/416* (2013.01); *A61Q 1/00* (2013.01); *A61Q 5/06* (2013.01); *A61Q 17/04* (2013.01); *A61K 2800/48* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 3,840,401 | A | 10/1974 | Umezawa et al. | |
| 2018/0338894 | A1* | 11/2018 | Nöcker .................... | A61K 8/19 |

FOREIGN PATENT DOCUMENTS

| | | | |
|---|---|---|---|
| FR | 2 984 147 | A1 | 6/2013 |

OTHER PUBLICATIONS

International Search Report mailed Mar. 19, 2021, issued in corresponding International Application No. PCT/EP2020/086704, filed Dec. 17, 2020, 2 pages.
Bouillon C. and Wikinson J., "The Science of Hair Care", 2nd edition, Taylor & Francis Edition. 2005, pp. 206.

* cited by examiner

*Primary Examiner* — Nannette Holloman
(74) *Attorney, Agent, or Firm* — CHRISTENSEN O'CONNOR JOHNSON KINDNESS PLLC

(57) ABSTRACT

The invention relates to a method for the cosmetic treatment of keratin materials, in particular human keratin materials, such as the skin or hair, comprising a stage of application of a composition comprising a compound of a metal belonging to the group of the rare earth metals, followed by a stage of application of an alkaline composition.

12 Claims, No Drawings

METHOD FOR THE COSMETIC TREATMENT OF KERATIN MATERIALS EMPLOYING A RARE EARTH METAL COMPOSITION AND AN ALKALINE COMPOSITION

The invention relates to a method for the cosmetic treatment of keratin materials, in particular human keratin materials, such as the skin or hair, comprising a stage of application of a composition comprising a specific metal compound, followed by a stage of application of an alkaline composition.

Many people wish to modify the shape of their head of hair or to introduce a cosmetic effect onto their skin.

As regards the head of hair, the existing solution consists in styling the hair, for example using a brush or a comb, to give the head of hair the desired shape. Nevertheless, this operation alone is not sufficient, the hairstyle having a tendency to hang down under the effect of the weight.

It is thus necessary in addition to fix the head of hair using products of lacquer or spray type. This method makes it possible to retain the shape of the head of hair for a few hours, indeed even a day.

Nevertheless, this effect is not lasting over time and requires repeating the styling and then fixing operations daily, indeed even washing the hair daily, before repeating these operations.

As regards the skin, it is known to apply cosmetic products, such as, for example, make-up products, products for protecting from UV radiation, in order to contribute a specific optical effect or also to conceal blemishes on the skin. Like the hair products, the hold of these products on the skin is also limited over time and it is necessary to reapply the product each day, indeed even several times during the day, in order to retain the cosmetic effect.

There thus exists a real need to develop methods for the cosmetic treatment of keratin materials, in particular human keratin materials, such as the skin or the hair, which are less restricting and which make it possible to produce cosmetic effects, such as styling effects or optical effects, which are lasting and which persist for one or more rinsing and/or washing operations.

It has been discovered, surprisingly, that a two-step cosmetic treatment method comprising a first stage of application, to the keratin materials, of a composition comprising at least one compound of a specific metal belonging to the group of the rare earth metals, followed by a second stage of application, to the said keratin materials, of an alkaline composition, makes it possible to achieve the above objectives, in particular in terms of durability of the effects during the day and of resistance of the effects to washing operations, up to at least 10 washing operations, making it possible to retain the effect beyond a week.

A subject-matter of the invention is thus a method for the cosmetic treatment of keratin materials, in particular human keratin materials, such as the hair, comprising:

a) a first stage of application, to the said keratin materials, of a composition (A) comprising one or more compounds of a metal belonging to the group of the rare earth metals, then b) a second stage of application, to the said keratin materials, of a composition (B) comprising one or more alkaline agents.

The method according to the invention makes it possible to produce, at the surface of keratin materials, such as the skin or hair, a durable inorganic coating conferring, on the said keratin materials, improved cosmetic performance qualities.

Thus, the method according to the invention makes it possible to contribute, to keratin fibres, such as the hair, a significant and durable styling effect, making it possible to reproduce a hairstyle simply, without having to re-wet the hair or put fixing product back on. The hair thus treated additionally exhibits a pleasant feel, without a cartonated effect. This effect is a lasting and resistant, in particular to washing.

The method according to the invention also makes it possible to contribute, to the skin, a lasting cosmetic effect, conferring a pleasant feel. This effect is also resistant to washing, in particular to several shampooing operations.

Other subject-matters, characteristics, aspects and advantages of the invention will become even more clearly apparent on reading the description and the examples which follow.

In the text which will follow, and unless otherwise indicated, the limits of a range of values are included in this range, in particular in the expressions “of between” and “ranging from . . . to . . . ”.

Moreover, the expression “at least one” used in the present description is equivalent to the expression “one or more”.

Composition (A)

The method according to the present invention comprises a first stage a) consisting in applying, to the keratin materials, in particular human keratin materials, for example the hair, a composition (A) comprising one or more compounds of a metal belonging to the group of the rare earth metals.

Compounds of a Metal Belonging to the Group of the Rare Earth Metals (Also Known as Rare Earth Metal Compound)

Mention may be made, as examples of a metal belonging to the group of the rare earth metals M, of scandium, yttrium, lanthanum, cerium, praseodymium, neodymium, promethium, samarium, europium, gadolinium, terbium, dysprosium, holmium, erbium, thulium, ytterbium and lutetium.

Preferably, the metal(s) belonging to the group of the rare earth metals are chosen from cerium, yttrium, ytterbium, lanthanum or europium.

According to a specific embodiment, the metal belonging to the group of the rare earth metals is in the +III form.

According to the invention, the compound of a metal belonging to the group of the rare earth metals is chosen from rare earth metal salts, rare earth metal complexes or rare earth metal oxides.

The rare earth metal salts according to the invention can be soluble or insoluble in the composition containing them.

Definition of the Rare Earth Metal Salts and Complexes

In the case of the salts and complexes of a rare earth metal according to the invention, the compound of a metal belonging to the group of the rare earth metals is in the +III oxidation state.

The metal M can then be combined, via its electron shell, with n1 anionic groups forming an ionic bond with M and/or with n2 groups forming a coordination bond with M. The groups forming a coordination bond are groups having a donor pair, such as carbonyl or amine, for example.

- If $n2=0$, the compound of a metal belonging to the group of the rare earth metals forms a salt and, in this case, the metal M is combined with 3 anionic groups.
- If $n2>0$, the compound of a metal belonging to the group of the rare earth metals forms a complex and, in this case, the number of anionic groups n1 can vary from 0 to 3.

The metal M is combined with one or more anionic groups and/or one or more groups forming a coordination bond.

Subsequently, the term "ligand" is understood to mean an ion or a molecule carrying a group which is combined, via an ionic bond or a coordination bond, with the metal M. One and the same ligand can carry several groups.

The term "rare earth metal compound" is understood to mean the combination of the metal M with its ligand(s).

A definition of the salts or complexes of rare earth metals can be found in the document: *Progress in the Science and Technology of the Rare Earths*, Volume 1, edited by Leroy Eyring in 1964, published by Macmillan Company and written by F. Gaume-Mahn, page 259 et seq.

Ligands Combined with the Rare Earth Metals M to Form a Salt or a Complex and Corresponding Rare Earth Metal Compounds Typically, the ligand can be a monoatomic or non-monoatomic monoanionic ion, such as a nitrate or a hydroxide ($OH^-$) or a halide (typically chloride or bromide). By way of example, the rare earth metal compound which results therefrom can then be $MCl_3$, $M(OH)_3$, $M(NO_3)_3$ and the like and in particular $Ce(NO_3)_3$, $Y(NO_3)_3$, $La(NO_3)_3$, $CeCl_3$, $YCl_3$ or $LaCl_3$.

The ligand can be a di- or trianionic ion, such as phosphate or sulfate. Mention may be made, by way of example, of the rare earth metal compounds such as $MPO_4$ or $M_2(SO_4)_3$ and in particular $CePO_4$, $YPO_4$, $LaPO_4$, $Ce_2(SO_4)_3$, $Y_2(SO_4)_3$ or $La_2(SO_4)_3$.

The ligand can contain one or more groups forming a coordination bond and a functional group forming an ionic bond.

Thus, the ligand can be a mono- or polycarboxylate molecule, such as acetate or succinate. In this case, it is considered that the carboxylate functional group acts as anionic group, via the hydroxyl of the carboxyl group, and acts as group forming a coordination bond, via the doublet of the oxygen of the carbonyl functional group. Thus, the resulting rare earth metal compound can be $M(R—(COO)_n)_{3/n}$. The ligand can, in addition to carrying one or more carboxylates, comprise other functional groups, such as hydroxyls or amines. Thus, the ligand may be in the form of hydroxycarboxylic acids or aminocarboxylic acids. Mention may be made, as mono- or polycarboxylic compound carrying additional functional groups, of tartrate, citrate, glycolate or ethylenediaminetetraacetate (EDTA) ions.

The ligand can carry a non-localized anionic charge, such as, for example, acetylacetonate. The rare earth metal compound will then be $M(acetylacetonate)_3$ or $M(acetylacetonate)_3.7H_2O$ where each acetylacetonate is bonded to the metal M by its two carbonyl functional groups, one acting as anionic group and the other as group which is bonded by coordination.

It can also be of the aromatic type, such as a phenol, a cyclopentadiene (*Progress in the Science and Technology of the Rare Earths*, edited by Leroy Eyring and written by F. Gaume-Mahn, page 296) or a pyridine.

The rare earth metal compound can comprise one or more ligands forming a coordination bond and one or more ligands forming an ionic bond. Thus, the rare earth metal compound can be yttrium dihydroxyacetate $Y((OH)_2acetate)$ (*Synthesis and Properties of Yttrium Hydroxyacetate Sols* by S. S. Balabanov, E. M. Gavrishchuk and D. A. Permin, published in the review *Inorganic Materials,* 2012, Vol. 48, No. 5, pp. 500-503, in 2012).

The rare earth metal compound can be a double salt, for example with a rare earth metal M and another cation different from the rare earth metals, such as, for example, an alkali metal ($Li,Ce(SO_4)_2$) or an alkaline earth metal or an organic cationic entity, such as a quaternary amine, such as an alkylpyridinium group.

These rare earth metal compounds, which are often highly hygroscopic, can be in the form of hydrates, such as, for example, $CeCl_3.7H_2O$; $YCl_3.6H_2O$; $LaCl_3.7H_2O$; $Ce(acetonate)_3.xH_2O$.

Oxides of Rare Earth Metals

Oxides of rare earth metals are known from the state of the art.

In the case of the oxides of rare earth metals according to the invention, the compound of a metal belonging to the group of the rare earth metals is in the +IV oxidation state in the specific case of cerium oxides and in the +III oxidation state for the other rare earth metals as defined above.

Mention may be made, by way of oxide, of the oxides of cerium ($CeO_2$), of lanthanum ($La_2O_3$), of yttrium ($Y_2O_3$), of erbium ($Er_2O_3$), of scandium ($Sc_2O_3$), of ytterbium ($Yb_2O_3$) or of europium ($Eu_2O_3$), preferably the oxides of cerium or of lanthanum. Preferably, the oxides of rare earth metals of use are cerium oxide, lanthanum oxide and yttrium oxide.

Preferably, the compound of a metal belonging to the group of the rare earth metals is dissolved in the composition (A).

Advantageously, the content of the metal compound(s) ranges from 0.05% to 25% by weight, preferably from 0.5% to 15% by weight, with respect to the total weight of the composition (A).

The composition (A) is preferably aqueous, alcoholic or aqueous/alcoholic.

When the composition (A) is aqueous, it preferably comprises water at a content of greater than or equal to 50% by weight, more preferentially of greater than or equal to 70% by weight, more preferentially still of greater than or equal to 90% by weight, with respect to the total weight of the composition (A).

When the composition (A) is alcoholic or aqueous/alcoholic, it can in particular comprise one or more organic solvents, preferably in a content ranging from 0.05% to 95% by weight and more preferentially from 1% to 70% by weight, with respect to the total weight of the composition (A).

This organic solvent can be a lower $C_2$ to $C_4$ alcohol, in particular ethanol and isopropanol, polyols and polyol ethers, such as propylene glycol, polyethylene glycol or glycerol. The organic solvent is preferably ethanol.

Preferably, the composition (A) exhibits an acidic pH. In other words, the pH of the composition (A) is less than 7, and preferably less than or equal to 5. More preferentially, the pH of the composition (A) is between 2 and 7, more preferentially still between 2 and 5.

Composition (B)

The method according to the present invention additionally comprises a second stage b) which consists in applying, to the keratin materials, in particular human keratin materials, such as the skin or the hair, a composition (B) comprising one or more alkaline agents.

Preferably, the alkaline agent(s) can be chosen from organic alkaline agents, inorganic alkaline agents, and their mixtures.

Preferably, the organic alkaline agent(s) are chosen from organic amines, the $pK_b$ of which at 25° C. is less than 12, more preferentially less than 10, more advantageously still less than 6. It should be noted that it is the $pK_b$ corresponding to the functional group of highest basicity. In addition, the organic amines do not comprise an alkyl or alkenyl fatty chain comprising more than ten carbon atoms.

The organic alkaline agent(s) are preferably chosen from alkanolamines, in particular mono-, di- or trihydroxy($C_1$-$C_6$)alkylamines, such as 2-amino-2-methylpropanol, oxyethylenated and/or oxypropylenated ethylenediamines, amino acids, the polyamines of following formula (II), and their mixtures:

(II)

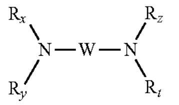

in which formula (II) W is a divalent $C_1$ to $C_6$ alkylene radical optionally substituted by one or more hydroxyl groups or a $C_1$ to $C_6$ alkyl radical and/or optionally interrupted by one or more heteroatoms, such as O or $NR_u$; $R_x$, $R_y$, $R_z$, $R_t$ and $R_u$, which are identical or different, represent a hydrogen atom, a $C_1$ to $C_6$ alkyl radical or a $C_1$ to $C_6$ hydroxyalkyl radical or a $C_1$ to $C_6$ aminoalkyl radical.

Mention may be made, as examples of amines of formula (II), of 1,3-diaminopropane, 1,3-diamino-2-propanol, spermine and spermidine.

The term "alkanolamine" is understood to mean an organic amine comprising a primary, secondary or tertiary amine functional group and one or more linear or branched $C_1$ to $C_8$ alkyl groups carrying one or more hydroxyl radicals.

Organic amines chosen from alkanolamines, such as mono-, di- or trialkanolamines, comprising from one to three identical or different $C_1$ to $C_4$ hydroxyalkyl radicals are suitable in particular for the implementation of the invention.

Mention may be made, among compounds of this type, of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol or tris(hydroxymethyl)aminomethane.

More particularly, the amino acids which can be used are of natural or synthetic origin, in their L, D or racemic form, and comprise at least one acid functional group chosen more particularly from carboxylic acid, sulfonic acid, phosphonic acid and phosphoric acid functional groups. The amino acids can be in neutral or ionic form.

Advantageously, the amino acids are basic amino acids comprising an additional amine functional group optionally included in a ring or in a ureido functional group.

Such basic amino acids are preferably chosen from those corresponding to the following formula (III), and also their salts:

$$R—CH_2—CH(NH_2)—C(O)—OH \quad (III)$$

in which formula (III) R represents a group chosen from imidazolyl, preferably imidazolyl-4-yl, aminopropyl, aminoethyl, $—(CH_2)_2N(H)—C(O)—NH_2$ and $—(CH_2)_2—N(H)—C(NH)—NH_2$.

Preference will be given, as basic amino acid, to lysine, arginine and proline.

The organic amine can also be chosen from organic amines of heterocyclic type. Mention may in particular be made, besides histidine, already mentioned in the amino acids, of pyridine, piperidine, imidazole, triazole, tetrazole and benzimidazole.

The organic amine can also be chosen from amino acid dipeptides. Mention may in particular be made, as amino acid dipeptides which can be used in the present invention, of carnosine, anserine and balenine.

The organic amine can also be chosen from compounds comprising a guanidine functional group. Mention may in particular be made, as amines of this type which can be used in the present invention, besides arginine, already mentioned as amino acid, of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Mention may be made, as hybrid compounds, of the salts of the abovementioned amines with acids, such as carbonic acid or hydrochloric acid.

Guanidine carbonate or monoethanolamine hydrochloride can be used in particular.

The inorganic alkaline agent(s) are preferably chosen from ammonia; alkanolamines; alkali metal carbonates and bicarbonates, such as sodium and potassium carbonates or bicarbonates; phosphates and hydrogenphosphates, such as sodium and potassium phosphates and hydrogenphosphates; inorganic hydroxides; and the mixtures of these compounds.

The inorganic hydroxides can be chosen from alkali metal, alkaline earth metal or transition metal hydroxides. Mention may be made, as inorganic hydroxides, for example, of sodium hydroxide, potassium hydroxide, lithium hydroxide, calcium hydroxide, magnesium hydroxide, barium hydroxide, strontium hydroxide, manganese hydroxide or zinc hydroxide.

The preferred hydroxide compounds are sodium hydroxide, potassium hydroxide, calcium hydroxide and lithium hydroxide, and more preferentially sodium hydroxide.

Preferably, the alkaline agent(s) are chosen from alkanolamines, such as monoethanolamine, ammonia and alkali metal carbonates and bicarbonates, such as sodium, potassium or ammonium carbonate or bicarbonate, and the mixtures of these compounds.

Advantageously, the composition (B) exhibits a pH of greater than 7, preferably of between 8 and 10.

Advantageously, the content of the alkaline agent(s) ranges from 0.05% to 25% by weight, preferably from 0.5% to 15% by weight, with respect to the total weight of the composition (B).

The composition (B) is preferably aqueous or aqueous/alcoholic.

When the composition (B) is aqueous, it preferably comprises water at a content of greater than or equal to 50% by weight, more preferentially of greater than or equal to 70% by weight, and more preferentially still of greater than or equal to 90% by weight, with respect to the total weight of the composition (B).

When the composition (B) is aqueous/alcoholic, it can in particular comprise one or more organic solvents, preferably in a content ranging from 0.05% to 95% by weight and more preferentially from 1% to 70% by weight, with respect to the total weight of the composition (B).

This organic solvent can be a lower $C_2$ to $C_4$ alcohol, in particular ethanol and isopropanol, polyols and polyol ethers, such as propylene glycol, polyethylene glycol or glycerol. The organic solvent is preferably ethanol.

The Thickening Agents

The composition (A) employed in the first stage a) and/or the composition (B) employed in the second stage b) of the method for the treatment of keratin materials according to the present invention can additionally comprise one or more thickening agents.

The thickening agent(s) can be of inorganic or organic origin.

The inorganic thickening agents can in particular be chosen from organophilic clays, fumed silicas or their mixtures.

The organophilic clay can be chosen from montmorillonite, bentonite, hectorite, attapulgite, sepiolite and their mixtures. The clay is preferably a bentonite or a hectorite.

These clays can be modified with a chemical compound chosen from quaternary amines, tertiary amines, amine acetates, imidazolines, amine soaps, fatty sulfates, alkylarylsulfonates, amine oxides, and their mixtures.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; or quaternium-18/benzalkonium bentonites, such as those sold under the names Claytone HT and Claytone PS by Southern Clay.

The fumed silicas can be obtained by high-temperature pyrolysis of a volatile silicon compound in an oxyhydrogen flame, producing a finely divided silica. This process makes it possible in particular to obtain hydrophilic silicas which exhibit a large number of silanol groups at their surface. Such hydrophilic silicas are sold, for example, under the names Aerosil 130®, Aerosil 200®, Aerosil 255®, Aerosil 300® and Aerosil 380® by Degussa, and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the silica by chemical reaction for the purpose of reducing the number of silanol groups. It is possible in particular to replace silanol groups with hydrophobic groups: a hydrophobic silica is then obtained.

The hydrophobic groups can be:

- trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by Degussa and Cab-O-Sil TS-530® by Cabot.
- dimethylsilyloxyl or polydimethylsiloxane groups, which are obtained in particular by treating fumed silica in the presence of polydimethylsiloxane or dimethyldichlorosilane. Silicas thus treated are known as Silica dimethyl silylate according to the CTFA (6th Edition, 1995). They are sold, for example, under the references Aerosil R972® and Aerosil R974® by Degussa, and Cab-O-Sil TS-610® and Cab-O-Sil TS-720® by Cabot.

The fumed silica preferably exhibits a particle size which can be nanometric to micrometric, for example ranging from approximately 5 to 200 nm.

The organic thickening agents can in particular be chosen from fatty acid amides (coconut acid diethanolamide or monoethanolamide, oxyethylenated alkyl ether carboxylic acid monoethanolamide), polymeric thickeners, such as cellulose thickeners (hydroxyethylcellulose, hydroxypropylcellulose, carboxymethylcellulose), guar gum and its derivatives (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic regions, and hydrophobic regions having a fatty chain (alkyl or alkenyl chain comprising at least 10 carbon atoms) which are capable, in an aqueous medium, of reversibly associating with one another or with other molecules).

Advantageously, when they are present in the composition (A) according to the invention, the content of the thickening agent(s) ranges from 0.02% to 2% by weight, with respect to the total weight of the composition (A).

Advantageously, when they are present in the composition (B) according to the invention, the content of the thickening agent(s) ranges from 0.1% to 5% by weight, with respect to the total weight of the composition (B).

The Additives

The composition (A) and/or the composition (B) according to the present invention can optionally additionally comprise one or more additives, other than the compounds of the invention, among which mention may be made of cationic, non-ionic, amphoteric or zwitterionic surfactants, and their mixtures, cationic, anionic, non-ionic or amphoteric polymers, or their mixtures, antidandruff agents, anti-seborrhoeic agents, vitamins and provitamins, including panthenol, sunscreens, sequestering agents, plasticizers, solubilizing agents, acidifying agents, antioxidants, hydroxy acids, fragrances and preservatives.

Of course, a person skilled in the art will take care to choose this or these optional additional compounds so that the advantageous properties intrinsically associated with the composition according to the invention are not, or not substantially, detrimentally affected by the envisaged addition(s).

The above additives can generally be present in an amount of, for each of them, between 0% and 20% by weight, with respect to the total weight of the composition (A) and/or of the composition (B).

Implementation of the Method

The method for the cosmetic treatment of keratin materials, in particular human keratin materials, such as the skin and the hair, according to the present invention comprises:

a) a first stage of application, to the said keratin materials, of a composition (A) comprising one or more compounds of a metal belonging to the group of the rare earth metals, then b) a second stage of application, to the said keratin materials, of a composition (B) comprising one or more alkaline agents.

In other words, stage b) is carried out after stage a).

According to the invention, stage b) is carried out following stage a), i.e. stage b) is carried out in a period of time preferably of less than or equal to 1 hour after stage a), preferably of less than or equal to 30 minutes, more preferentially of less than or equal to 15 minutes. According to one embodiment, the composition (A) and the composition (B) are applied simultaneously. According to another embodiment, a leave-on time of between 1 and 20 minutes is applied between the application of the composition (A) and the application of the composition (B).

The composition (A) according to the invention can be applied to dry or wet keratin materials.

According to an alternative form, the method according to the invention employs a stage of intermediate drying, with or without heating means, of the keratin materials between stages a) and b).

According to a second alternative form, the composition (B) is applied directly after application of the composition (A), that is to say that stages a) and b) are carried out successively without a leave-on time and without an intermediate stage of rinsing of the keratin materials.

Preferably, when the keratin materials are hair, the method can additionally comprise a stage of superficially drying the hair between stages a) and b).

Advantageously, the method according to the invention additionally comprises, following stage b), a stage of final washing and/or rinsing of the keratin materials.

Preferably, after application of the composition (B), a leave-in time which can range from 1 to 15 minutes, preferably from 2 to 10 minutes, is applied before rinsing and/or washing of the keratin materials.

The following examples serve to illustrate the invention without, however, exhibiting a limiting nature.

EXAMPLES

In the examples which follow, all the amounts are shown, unless otherwise indicated, as percentage by weight of active material, with respect to the total weight of the composition.

Example 1: Method for the Treatment of the Hair

Compositions

Compositions A1, A2, A3 and B1 to B4 were prepared from the ingredients, the contents of which are shown as active material in the tables below:

TABLE 1

| | Compositions A | | |
|---|---|---|---|
| Ingredients | A1 | A2 | A3 |
| Cerium chloride•$7H_2O$ (Sigma-Aldrich) | 5 | — | — |
| Lanthanum chloride•$7H_2O$ (Sigma-Aldrich) | — | 5 | — |
| Yttrium hydroxyacetate | — | — | 5 |
| Water | q.s. for 100 | q.s. for 100 | q.s. for 100 |

TABLE 2

| Ingredients | B1 |
|---|---|
| 20% Aqueous ammonia | 25 |
| Water | q.s. for 100 |

Procedure

Locks of 2.7 g of bleached hair are styled/shaped beforehand.

The first three locks L1, L2 and L3 are treated with 0.75 g of composition A1, A2 and A3 per lock.

After a leave-in time of 15 minutes, the locks L1, L2 and L3 are subsequently treated, without intermediate rinsing, with 0.75 g of composition B1 per lock, followed by a leave-in time of 15 minutes.

The locks are subsequently washed/rinsed/superficially dried.

At the same time, three other locks L1', L2' and L3' are treated with 0.75 g of composition B1 per lock.

After a leave-in time of 15 minutes, the locks L1', L2' and L3' are subsequently treated, without intermediate rinsing, with 0.75 g of composition A1, A2 and A3 per lock, followed by a leave-in time of 15 minutes.

The locks are subsequently washed/rinsed/superficially dried.

Evaluation and Results

After free drying, the locks are evaluated visually. The cartonating effect is evaluated, which effect corresponds to the presence of zones in the lock where the hairs are stuck to one another or the absence of such stiff zones. If the lock does not exhibit cartonating zones, the grade is 0. If the lock is completely covered with cartonating zones, the grade is 5. The evaluations are carried out by steps of 0.5 point.

The evaluation of the locks L1, L2, L3, L1', L2' and L3' and an untreated lock L0 shows a reduction in the cartonating effect when the protocol according to the invention is followed.

TABLE 3

| Lock | LI | L1' | L2 | L2' | L3 | L3' |
|---|---|---|---|---|---|---|
| | 0 | 3 | 0 | 2 | 2 | 3 |

Example 2: Method for the Treatment of the Hair

Demonstration of the Styling Effect and its Persistence

Procedure

Malleable heads are prepared by cutting the hair with a mid-length cut (thus arriving at the base of the neck).

On a first malleable head H1, an application is carried out on the right half head according to the following procedure:

1. 1 g of composition A1 is applied with a pipette at the roots and then the hair is combed from the root to the ends in order to cause the composition to penetrate and to spread it. This is repeated nine times in a row, care being taken to treat the majority of the hairs of this part of the malleable head.

2. Then, after a leave-on time of 15 minutes, the composition B1 is applied on the same part of the malleable head in a proportion of 2 g of composition B1. This application is repeated 10 times in total. Then, after a leave-on time of 15 minutes, the head of hair is copiously rinsed.

On the same head H1, the application is carried out on the left half-head according to the same process as before, except that the composition A1 is replaced by the composition A0, a composition comprising only water.

Evaluation and Results

A first evaluation is carried out.

To do this, the starting point is to dry the hair with a hairdryer, without carrying out blow drying (drying is carried out by the simple effect of the air of the hairdryer). Combing is then carried out, while trying to place the hair horizontally. To do this, each lock is taken in the teeth of the comb at the root and then the comb is slid towards the ends while forcing the hair towards the back.

It is observed that, in the two parts of the malleable head, the hair is indeed positioned (hair at the back) but, as soon as the hair is no longer held by the teeth of the comb, the shape given to the left half-head does not hold. The hair falls virtually immediately. Conversely, the shape given to the right half-head holds well; the hair remains in place towards the back of the head.

The same malleable head is washed five times. After each washing operation, the hold of the shaping of the hair towards the back of the head is evaluated.

There is again observed, on the left half-head, a difficulty in retaining the shape of the styled hair towards the back. On the right side of the malleable head, the possibility is observed of positioning the hair at the back in a lasting manner. After five other washing operations, as it is observed on the right side that the hold of the shape of the hairstyle towards the back of the head decreases, the treatment described above is again carried out in order to reactivate the possibility of the hair being styled at the back.

Example 3: Method for the Treatment of the Hair

Compositions

Compositions B2, B3 and B4 were prepared from the ingredients, the contents of which are shown as active material in the tables below:

TABLE 4

| | Compositions B | | | |
|---|---|---|---|---|
| Ingredients | B2 | B3 | B4 | B0 |
| Ammonia (20% in water) | 10% | — | | — |
| Sodium bicarbonate | — | 10% | — | — |
| 10% Sodium hydroxide in water | — | — | 10% | — |
| pH | 11.2 | 8.3 | 13.2 | 6.9 |
| Water | q.s. for 100 | q.s. for 100 | q.s. for 100 | q.s. for 100 |

Procedure

The same protocol as described for Example 2 is carried out.

On a malleable head H2, the protocol starting from the composition A1 and then from the composition B2 is applied on the right half-head and the protocol consisting in applying the composition A1 and then the composition B0 is applied on the left half-head.

On a malleable head H3, the same protocol starting from the composition A1 and then from the composition B3 is applied on the right half-head and the protocol consisting in applying the composition A1 and then the composition B0 is applied on the left half-head.

Results

A much greater styling power is observed, on the malleable head H2, on the right than that observed on the left half-head. A styling power is observed, on the malleable head H3, which is greater on the right than that obtained on the left half-head.

Example 4

Procedure

The same test is carried out as in Example 2, except that the rare earth metal compound of the first composition is replaced using the compositions A2 or A3.

The composition A2 and then the composition B1 are applied on the right half-head on a malleable head H4 and then rinsing is carried out. The composition A2 and then the composition B0 are applied on the left half-head and then rinsing is carried out.

The composition A3 and then the composition B1 are applied on the right half-head on a malleable head H5 and then rinsing is carried out. The composition A3 and then the composition B0 are applied on the left half-head and then rinsing is carried out.

Results

An ease of styling is observed on the right on the malleable head H4, making it possible to place the hair at the back.

An ease of styling is observed on the right on the malleable head H5.

Example 5

Compositions

The following comparative composition A4 is produced:

TABLE 5

| Ingredients | A4 |
|---|---|
| Calcium chloride dihydrate (Sigma-Aldrich) | 10% |
| Water | q.s. for 100 |

Procedure

The same test is carried out as in Example 2, except that the composition A1 and then the composition B1 are applied on the right half-head on a malleable head H6 and then rinsing is carried out. The composition A4 and then the composition B1 are applied on the left half-head and then rinsing is carried out.

Results

Retention of the shaping carried out at the time of the styling is observed on the right half-head: the hair remains positioned on the back of the head. Styling power is not encountered on the left half-head.

The invention claimed is:

1. A method for the cosmetic treatment of human keratin materials for forming a durable inorganic coating film at the surface of said keratin materials, the method comprising:

a) a first stage of application, to the said keratin materials, of a composition (A) having an acidic pH and comprising from 0.5% to 15% by weight, with respect to the total weight of the composition (A), of one or more compounds of a metal belonging to the group of the rare earth metals, then b) a second stage of application, to the said keratin materials, of a composition (B) comprising one or more alkaline agents.

2. The method according to claim 1, characterized in that the metal of the metal compound(s) is chosen from cerium, yttrium, ytterbium, lanthanum or europium.

3. The method according to either claim 1, characterized in that the metal belonging to the group of the rare earth metals is in the +III oxidation state.

4. The method according to claim 1, characterized in that the metal compound(s) are chosen from salts of rare earth metals, complexes of rare earth metals or oxides of rare earth metals.

5. The method according to claim 1, characterized in that the metal compound(s) are chosen from yttrium dihydroxyacetate, cerium chloride, yttrium chloride, lanthanum chloride, Ce(acetonate)$_3$, cerium oxide, lanthanum oxide, yttrium oxide, erbium oxide, scandium oxide, ytterbium oxide, europium oxide, and their mixtures.

6. The method according to claim 1, characterized in that the composition (A) exhibits an acidic pH of between 2 and 5.

7. The method according to claim 1, characterized in that the alkaline agent(s) are chosen from alkanolamines, ammonia alkali metal carbonates and bicarbonates, and the mixtures of these compounds.

8. The method according to claim 1, characterized in that the content of the alkaline agent(s) ranges from 0.05% to 25% by weight, with respect to the total weight of the composition (B).

9. The method according to claim 1, characterized in that the composition (B) exhibits a pH of between 8 and 10.

10. The method according to claim 1, characterized in that the composition (A) and/or the composition (B) additionally comprises one or more thickening agents.

11. The method according to claim 1, characterized in that stages a) and b) are carried out successively without an intermediate stage of rinsing of the keratin materials.

12. The method according to claim 1, characterized in that stage b) is followed by a stage of final washing and/or rinsing of the said keratin materials.

* * * * *